United States Patent
Drew et al.

(10) Patent No.: US 8,500,499 B2
(45) Date of Patent: Aug. 6, 2013

(54) CONTACT ASSEMBLIES FOR MEDICAL DEVICES HAVING RESILIENT CONTACT MEMBERS MOUNTED IN CHANNELS OF A MOUNTING MEMBER

(75) Inventors: Michael H. Z. Drew, Maple Grove, MN (US); Michael J. Elvidge, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/388,474

(22) PCT Filed: Aug. 4, 2010

(86) PCT No.: PCT/US2010/044412
§ 371 (c)(1),
(2), (4) Date: Feb. 2, 2012

(87) PCT Pub. No.: WO2011/017432
PCT Pub. Date: Feb. 10, 2011

(65) Prior Publication Data
US 2012/0129409 A1 May 24, 2012

Related U.S. Application Data

(60) Provisional application No. 61/231,480, filed on Aug. 5, 2009.

(51) Int. Cl.
*H01R 13/187* (2006.01)
(52) U.S. Cl.
USPC ........................................................ 439/843
(58) Field of Classification Search
USPC .............................. 439/843, 667–669; 29/857
See application file for complete search history.

(56) References Cited

U.S. PATENT DOCUMENTS

| | | | |
|---|---|---|---|
| 4,715,380 A | 12/1987 | Harris | |
| 4,934,366 A | 6/1990 | Truex et al. | |
| 4,966,564 A | 10/1990 | Foote | |
| 5,012,807 A | 5/1991 | Stutz, Jr. | |
| 5,076,270 A | 12/1991 | Stutz, Jr. | |
| 5,324,311 A | 6/1994 | Acken | |
| 6,662,035 B2 | 12/2003 | Sochor | |
| 6,725,096 B2 | 4/2004 | Chinn et al. | |
| 6,862,478 B1 | 3/2005 | Goldstein | |
| 6,895,276 B2 | 5/2005 | Kast et al. | |
| 7,047,077 B2 * | 5/2006 | Hansen et al. | 607/37 |
| 7,083,474 B1 * | 8/2006 | Fleck et al. | 439/668 |
| 7,110,827 B2 | 9/2006 | Sage et al. | |
| 7,167,749 B2 | 1/2007 | Biggs et al. | |
| 7,299,095 B1 | 11/2007 | Barlow et al. | |
| 7,510,447 B2 * | 3/2009 | Drew | 439/669 |
| 7,769,458 B2 | 8/2010 | Lahti et al. | |
| 7,769,459 B2 | 8/2010 | Balsells | |

(Continued)

*Primary Examiner* — Chandrika Prasad

(57) ABSTRACT

A contact assembly, which may be included in a connector assembly for a connector module of a medical device, includes one or more resilient contact members; each contact member may comprise a coiled wire having a first stiffness and a second stiffness. The assembly may further include a plug member associated with each contact member. Each contact member may be mounted in the assembly via insertion into a corresponding channel of a mounting member, such that a first terminal end of the contact member abuts a terminal surface of the channel. If included, the plug member makes electrical contact with a second terminal end of the inserted contact member, and is coupled to the mounting member. A contact surface of the mounted contact member is exposed within a connector bore of the mounting member, through an opening in the channel.

31 Claims, 10 Drawing Sheets

U.S. PATENT DOCUMENTS

| | | |
|---|---|---|
| 8,091,226 B2 | 1/2012 | Sjostedt |
| 8,250,752 B2 * | 8/2012 | Drew .............................. 29/857 |
| 2001/0049237 A1 * | 12/2001 | Saka et al. .................... 439/843 |
| 2003/0163171 A1 * | 8/2003 | Kast et al. ...................... 607/36 |
| 2004/0064164 A1 | 4/2004 | Ries et al. |
| 2005/0027325 A1 | 2/2005 | Lahti et al. |
| 2006/0063438 A1 * | 3/2006 | Dent .............................. 439/843 |
| 2008/0255631 A1 * | 10/2008 | Sjostedt et al. ................. 607/37 |

* cited by examiner

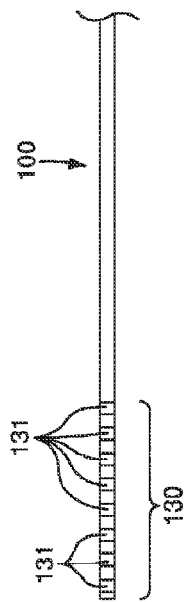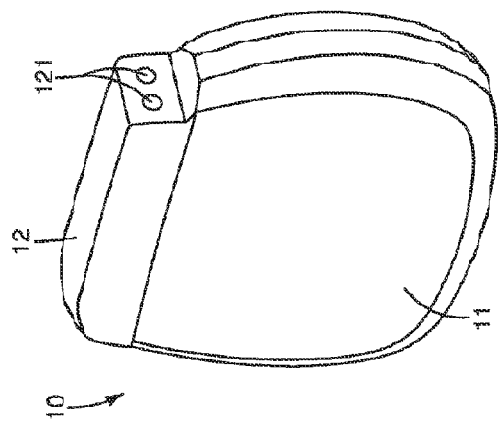
Figure 1A

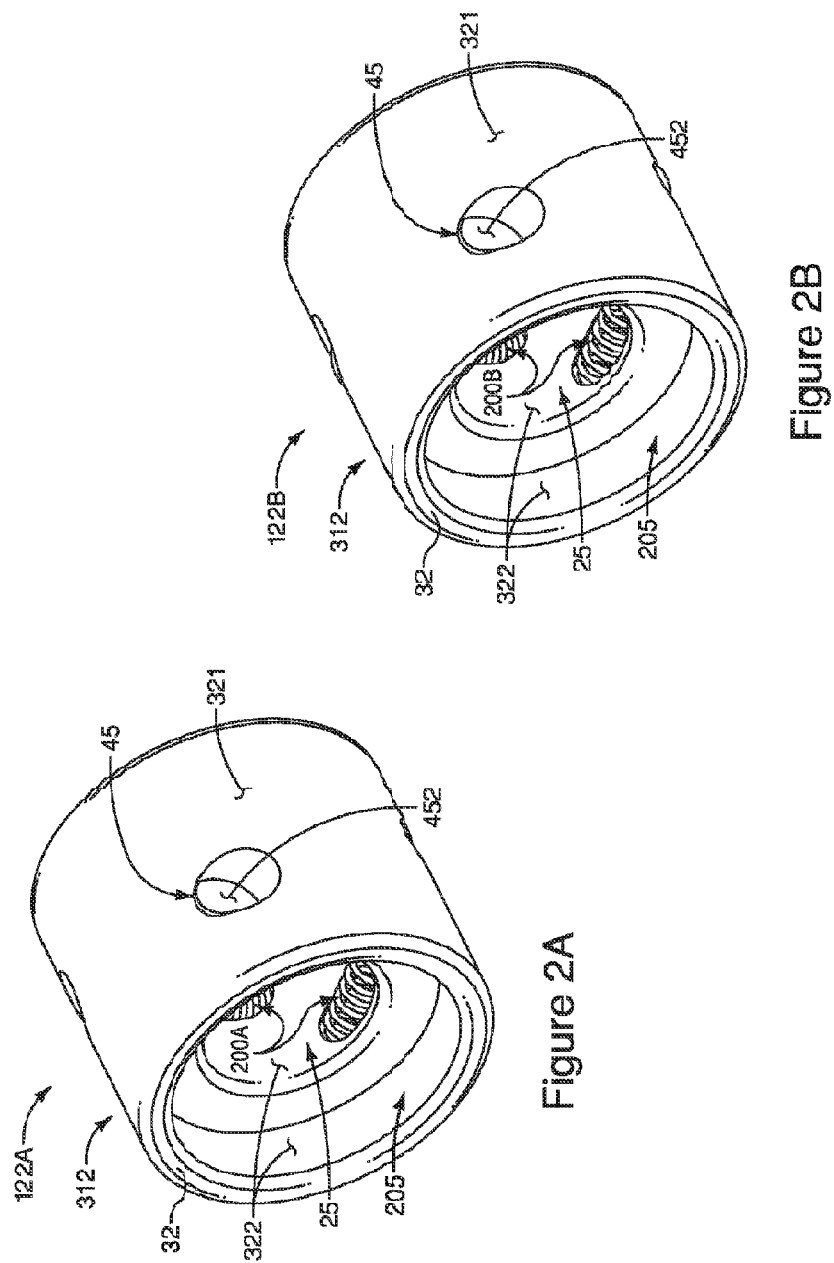

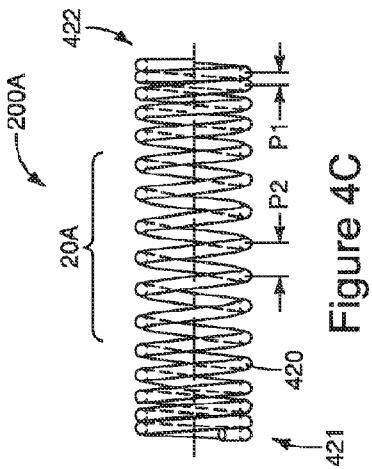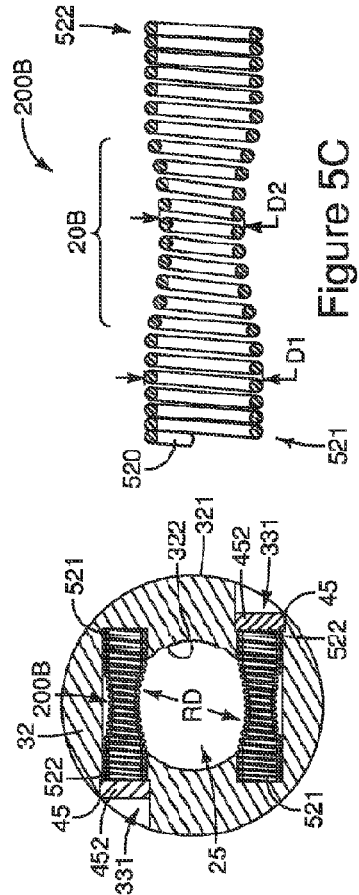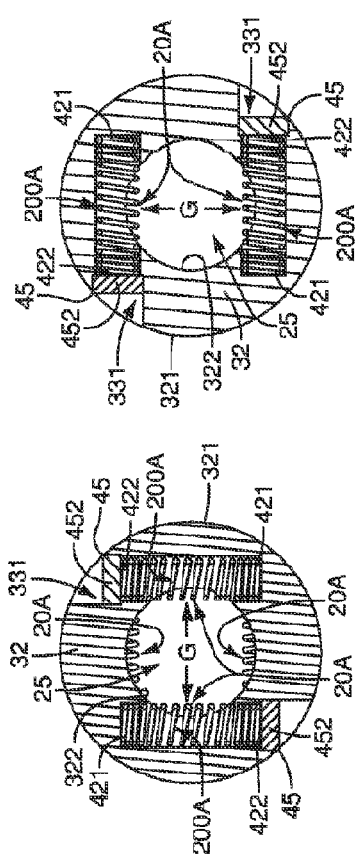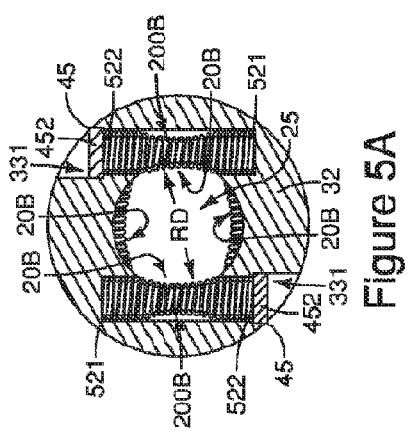

CONTACT ASSEMBLIES FOR MEDICAL DEVICES HAVING RESILIENT CONTACT MEMBERS MOUNTED IN CHANNELS OF A MOUNTING MEMBER

CROSS-REFERENCE TO RELATED APPLICATIONS

This application is a U.S. National Stage filing under 35 U.S.C. 371 of copending PCT Application Serial No. PCT/US2010/044412, filed Aug. 4, 2010, which claims priority to U.S. Provisional Patent Application No. 61/231,480, filed Aug. 5, 2009, which applications are hereby incorporated by reference as if re-written in their entirety.

TECHNICAL FIELD

The present disclosure pertains to medical devices and more particularly to medical device connector assemblies and contact assemblies thereof.

BACKGROUND

A host of medical devices include electrical connector assemblies for coupling with a type of medical electrical lead connector that is formed along a proximal portion of the lead; the lead connector includes a plurality of conductive surfaces, which are disposed along a length thereof and are spaced apart from one another. Device electrical connector assemblies typically include a plurality of electrical contacts positioned within a bore of what is typically called a device connector module, or header, a locations corresponding to the conductive surfaces of the lead connector, so that each electrical contact may electrically couple with the corresponding conductive surface, when the lead connector is fully inserted within the bore. Some device connector assemblies further include seal members, which are located between each adjacent pair of electrical contacts and are sized to seal against insulative surfaces located between the conductive surfaces of the lead connector, in order to provide electrical isolation for each electrical coupling. Although a variety of contact and connector assemblies for medical devices are known in the art, there is still a need for new contact assembly designs that provide for stable electrical connection without increasing a bulk, complexity or cost of device connector assemblies.

BRIEF DESCRIPTION OF THE DRAWINGS

The following drawings are illustrative of particular exemplary embodiments and therefore do not limit the scope of the invention. The drawings are not to scale (unless so stated) and are intended for use in conjunction with the explanations in the following detailed description. Embodiments of the present disclosure will hereinafter be described in conjunction with the appended drawings, wherein like numerals denote like elements.

FIG. 1A is perspective view of a portion of an exemplary medical system that may include embodiments of the present disclosure.

FIGS. 2A-B are perspective views of contact assemblies, according to alternative embodiments.

FIGS. 4A-B are section views of the contact assembly shown in FIG. 2A.

FIG. 4C is a plan view of a resilient contact member, according to some embodiments.

FIGS. 5A-B are section views of the contact assembly shown in FIG. 2B.

FIG. 5C is a section view of a resilient contact member, according to some alternate embodiments.

DETAILED DESCRIPTION

The following detailed description is exemplary in nature and is not intended to limit the scope, applicability, or configuration of embodiments disclosed herein. Rather, the following description provides practical illustrations for implementing exemplary embodiments. Examples of constructions, materials, dimensions, and manufacturing processes are provided for selected elements, and all other elements employ that which is known to those of skill in the field of the disclosure. Those skilled in the art will recognize that many of the examples provided have suitable alternatives that can be utilized.

Figure 1B:
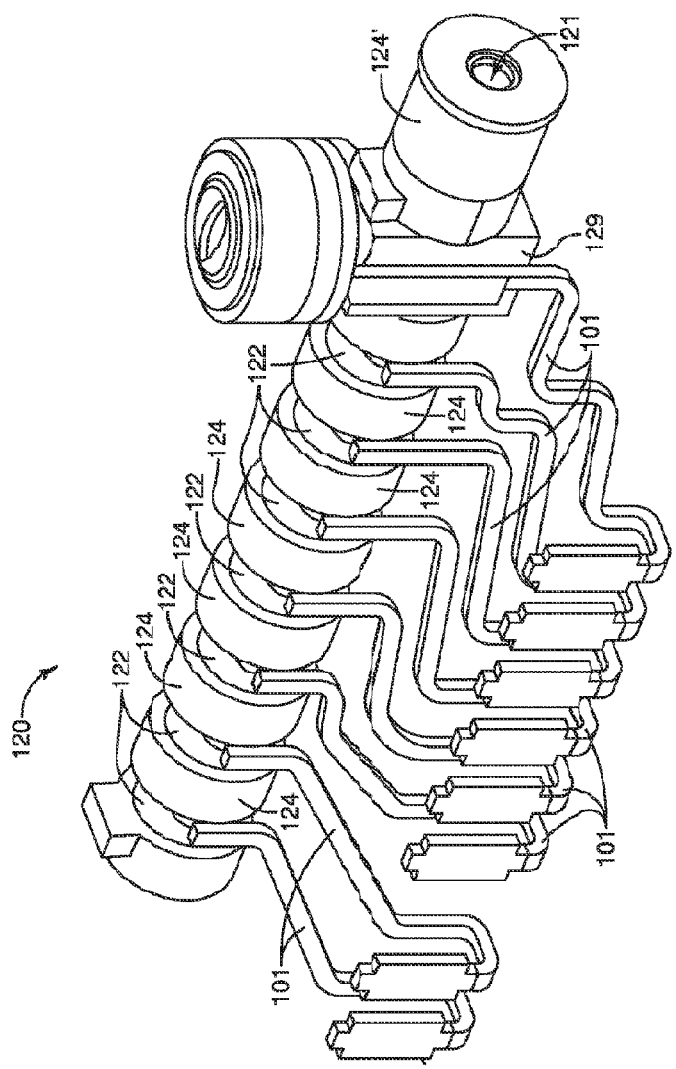
FIG. 1B is a perspective view of a device connector assembly, from the system show in FIG. 1A, according to an exemplary embodiment.

FIG. 1A is perspective view of a portion of an exemplary medical system that may include embodiments of the present disclosure. FIG. 1A illustrates the medical system including a medical device 10 and a medical electrical lead 100; a proximal end of lead 100 is shown terminated by a connector 130 which includes a plurality of conductive surfaces 131 spaced apart along a length thereof by a plurality of interposed insulative spacers. Materials, components and construction methods for lead connectors, such as connector 130, are well known to those skilled in the art. FIG. 1A further illustrates device 10 including a housing 11 and a connector module 12 mounted thereto; module 12 includes a pair of bores 121, each of which corresponds to a connector assembly 120 contained within module 12, for example, as shown in FIG. 1B.

FIG. 1B is a perspective view of connector assembly 120, according to an exemplary embodiment, separated from a sidewall of module 12. FIG. 1B illustrates connector assembly 120 including a plurality of contact assemblies 122, which are spaced apart from one another by a plurality of seal members 124, along a length of bore 121. Connector assembly 120 further includes a set screw-type contact 129, the construction of which is known to those skilled in the art. FIG. 1B further illustrates a plurality of conductive wires 101, one of wires 101 being coupled to contact 129, and each the rest of wires 101 being coupled to a corresponding contact assembly 122 of connector assembly 120, in order to provide electrical coupling between connector assembly 120 and device circuitry contained within housing 11 (FIG. 1A).

According to the illustrated embodiment, when lead connector 130 is fully inserted into bore 121, a location of each conductive surface 131 will correspond with one of contact assemblies 122 and contact 129, for electrical coupling therebetween, and interspersed seal members 124 will provide electrical isolation between the couplings. The section view of FIG. 7, which is described below, shows a portion of lead connector 130 inserted into bore 121. An additional sealing member 124', which is shown forming an entry into bore 121, may prevent an ingress of bodily fluids into bore 121, for example, if device 10 is an implantable device.

Those skilled in the art will appreciate that the sidewall of module 12 (FIG. 1A), for example, being formed from either silicone or polyurethane, or a combination thereof, may be molded around connector assemblies 120 and includes passages or wire-ways for the routing of conductive wires 101 from contact assemblies 122 to corresponding feedthrough ports, which extend through housing 11, according to designs known to those skilled in the art; if device 10 is implantable, the feedthrough ports are hermetically sealed. It should be noted that alternative connector assemblies, for example, which include a fewer or greater number of contact assemblies 122, are not outside the scope of the present disclosure; furthermore connector modules having a single bore, or more than two bores, rather than the pair of bores 121 shown in FIG. 1A, may employ embodiments of the present disclosure.

FIG. 2A is a perspective view of a first type of contact assembly 122, designated as 122A, according to some embodiments of the present disclosure; and FIG. 2B is a perspective view of a second type of contact assembly 122, designated as 122B, according to some alternative embodiments. FIGS. 2A-B illustrate each of contact assemblies 122A, 122B including a mounting member 312; mounting member 312 is shown including a sidewall 32, which has an outer surface 321 and an inner surface 322. Sidewall 32 of mounting member 312 may be formed from any suitable conductive material, examples of which include, without limitation, MP35N alloy, titanium and alloys thereof, tantalum and alloys thereof, platinum-iridium alloys and stainless steel. According to the illustrated embodiments, inner surface 322 defines a connector bore 25 and at least one counter bore 205; according to alternate embodiments, counter bore 205 need not be included. With reference back to FIGS. 1A-B, connector bore 25 is approximately aligned along one of module bores 121, when contact assembly 122A, 122B is part of one of connector assemblies 120. FIG. 2A further illustrates contact assembly 122A including resilient contact members 200A mounted within sidewall 32 of mounting member 312, while FIG. 2B further illustrates contact assembly 122B including resilient contact members 200B mounted within sidewall 32 of mounting member 312. Channels 310, which are formed in sidewall 32, for the mounting of contact members 200A, 200B, may be seen in FIGS. 3A-D; and, resilient contact members 200A, 200B may be seen in FIGS. 4A-C and 5A-C.

Figure 3B:
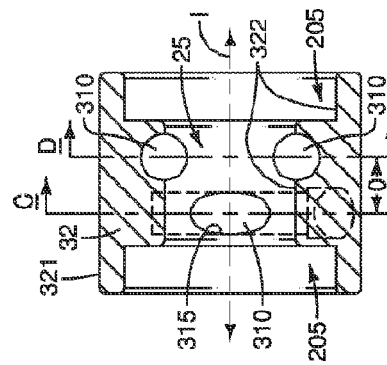
FIG. 3B is a section view, through section line B-B of FIG. 3A, according to some embodiments.
Figure 3D:
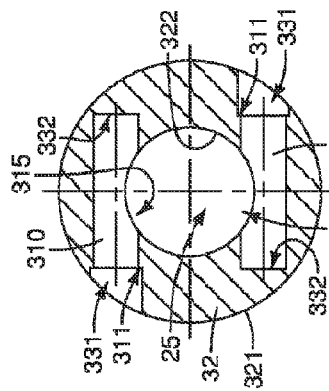
FIGS. 3C-D are section views, through section lines C-C and D-D, respectively, of FIG. 3B, according to some embodiments.
Figure 3A:
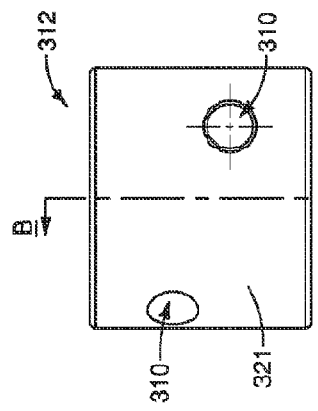
FIG. 3A is a plan view of a mounting member, which may be included in either of the contact assemblies of FIGS. 2A-B, according to some embodiments.
Figure 3C:
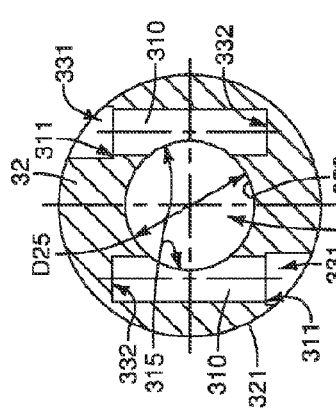

FIG. 3A is a plan view of mounting member 312, according to some embodiments; FIG. 3B is a section view, through section B-B of FIG. 3A, according to some embodiments; and, FIGS. 3C-D are section views, through section lines C-C and D-D, respectively, of FIG. 3B, according to some embodiments. FIGS. 3A-D illustrate four channels 310 formed in sidewall 32 of mounting member 312, between inner surface 322 and outer surface 321 thereof. Each channel 310 is shown including an entryway 331, which is located at outer surface 321 of sidewall 32, a terminal surface 332 and an opening 315, which is located at inner surface 322 of sidewall 32, between entryway 331 and terminal surface 332. According to the illustrated embodiment, either of contact members 200A, 200B may be mounted in mounting member 312 via insertion into entryway 331 of one of channels 310; once inserted, contact member 200A, 200B may be passed into the channel until a terminal end thereof abuts terminal surface 332, for example, as illustrated in FIGS. 4A-B and 5A-B.

First, with reference to FIGS. 4C and 5C, each of resilient contact members 200A, 200B is shown extending from a first terminal end 421, 521 thereof to a second terminal end 422, 522 thereof and including a contact surface 20A, 20B located between terminal ends 421, 521 and 422, 522. According to the illustrated embodiments, each of resilient contact members 200A, 200B is formed from a coiled wire 420, 520 whose outer surface serves as contact surface 20A, 20B; each contact surface 20A, 20B is exposed through opening 315 of the channel 310, in which contact member 200A, 200B is mounted, for example, as illustrated in FIGS. 4A-B and 5A-B, for electrical coupling with one of conductive surfaces 131 of lead connector 130 (FIG. 1A), when lead connector 130 is inserted through connector bore 25. Wire 420, 520 may have a diameter between approximately 0.002 inch and approximately 0.005 inch and may be formed from any suitable conductive material or combination of materials, examples of which include, without limitation, MP35N alloy, titanium and alloys thereof, tantalum and alloys thereof, and platinum-iridium alloys.

With further reference to FIGS. 3B-D, and to FIGS. 4A-B and 5A-B, each channel 310 of mounting member 312 extends across a longitudinal axis 1 of connector bore 25 such that each entryway 331 and corresponding terminal surface 332 are located on opposite sides of axis 1. Furthermore, with reference to FIGS. 3C, 4A and 5A, openings 315 of a first and a second of channels 310 are shown positioned directly opposite one another, and, with reference to FIGS. 3D, 4B and 5B, openings 315 of a third and a fourth of channels 310 are also shown positioned directly opposite one another. According to the illustrated embodiment, the openings 315 of the third and fourth channels (FIG. 3D) are rotated approximately ninety degrees from the openings 315 of the first and second channels (FIG. 3C), and are offset by a distance O (FIG. 3B), along longitudinal axis 1, from the openings of the first and second channels. Thus, it may be appreciated that, the arrangement of channel openings 315 enables contact surfaces 20A, 20B, which are exposed therethrough, for example, as illustrated in FIGS. 4A-B and 5A-B, to make symmetrical and stable contact with inserted lead connector 130, and to center connector 130 within connector bore 25. Furthermore, by successively centering connector 130 in each connector bore 25, for example, which are aligned along bore 121 of module 12 (FIG. 1A), this arrangement can increase the ease by which connector 130 is inserted into connector bore 121. Maintaining such a centering may be particularly important if the medical system includes multiple contact assemblies and corresponding connector conductive surfaces, for example, like that illustrated in FIGS. 1A-B, and/or if the lead connector is somewhat flexible, an attribute of some relatively small diameter connectors employed for medical electrical leads, such as lead 100. According to some exemplary embodiments, a diameter D25 of connector bore 25 is between approximately 0.055 inch and approximately 0.060 inch and distance O of the offset between openings 315 is between approximately 0.020 inch and approximately 0.025 inch.

Although the illustrated number and arrangement of contact surfaces 20A, 20B in contact assemblies 122A, 122B, which are facilitated by the number and arrangement of channels 310 in mounting member sidewall 32, provide the aforementioned advantages, alternate numbers and arrangements are not outside the scope of the present disclosure. For example, it is contemplated that the number and relative locations of the channels may be such that asymmetrical contact forces are imposed by corresponding mounted contact surfaces 20A, 20B on an inserted lead connector. An example of one such arrangement of channels in a mounting member 812 of a contact assembly 822, according to some alternate embodiments, will be described below, in conjunction with FIGS. 8A-B. Furthermore, a size of one of the channels and the corresponding contact member may differ from the rest.

With further reference to FIGS. 4A-B and 5A-B, each of contact assemblies 122A, 122B further include a plug member 452, which is shown fixed within entryway 331 of each channel 310, in order to hold each contact member 200A, 200B within the corresponding channel 310. According to the illustrated embodiments, each plug member 452 is electrically coupled to both the corresponding contact member 200A, 200B and to sidewall 32 of mounting member 312, for example, to the former, via a spring force that opposes the compression of contact member 200A, 200B within channel 310, and, to the latter, via a weld joint 45 formed, for example, by laser welding, in proximity to outer surface 321 of sidewall 32, respectively. A compression of contact member 200A, 200B, within channel 310, when plug member 452 is fixed within entryway 331, may also assure stable electrical contact between first terminal end 421, 521 and terminal surface 332 of channel 310. Thus, when lead connector 130 is inserted into connector bore 25 of either of contact assemblies 122A, 122B, such that one of the conductive surfaces 131 thereof (FIG. 1A) makes contact with conductive surface 20A, 20B of each contact member 200A, 200B, the electrical connection between mounting member 312 and conductive wire 101, for example, described in conjunction with FIG. 1B, will electrically connect the conductive surface 131 of lead connector 130 with the circuitry contained within device housing 11.

According to those embodiments that include weld joints 45, each well joint 45 may be formed about a portion or an entire perimeter of the corresponding plug member 452. According to some assembly methods of the present disclosure, after first terminal end 421, 521 of each contact member 200A, 200B is inserted into entryway 331 of the corresponding channel 310 and then passed into channel 310 to abut terminal surface 332 thereof, each plug member 452 is inserted into the corresponding entryway 331, so as to make electrical contact with second terminal end 422, 522 of the corresponding contact member 200A, 200B, and then each plug member 452 is coupled to sidewall 32. According to some alternate methods, each plug member 452 is coupled to second terminal end 422, 522 of the corresponding contact member 200A, 200B, for example, via another weld joint, prior to inserting first terminal end 421, 521 thereof into the corresponding channel 310 of mounting member 312.

Figure 4D:
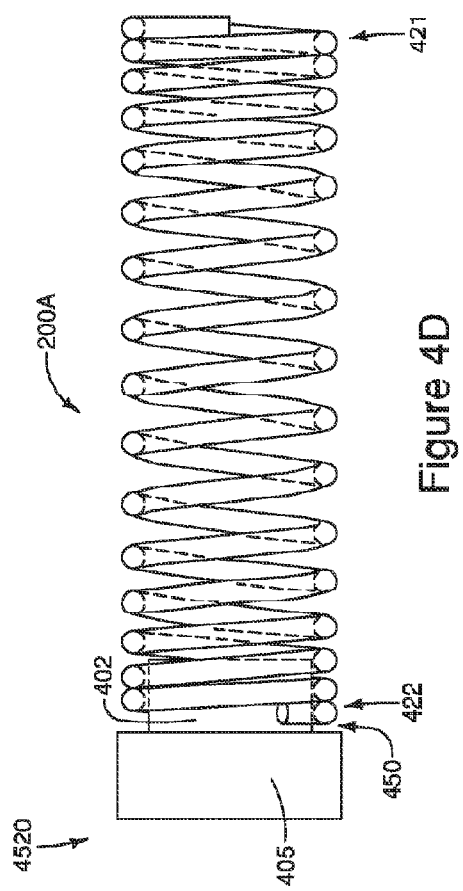
FIG. 4D is a plan view of the contact member, shown in FIG. 4C, assembled together with a plug member, according to some alternate embodiments.

According to some alternate embodiments, one or all of plug members 452 may include a pin extension for insertion within an inner diameter of the second terminal end 422, 522 of the corresponding contact member 200A, 200B. For example, FIG. 4D is a plan view of contact member 200A assembled together with a plug member 4520, wherein plug member 4520 includes a head 405 and a pin extension 402; head 405 has a diameter sized to fit within entryway 331 of channel 310, as previously shown for plug member 452, and pin extension 402 has a diameter sized to fit within an inner diameter of second terminal end 422 of contact member 200A, as shown. According to the illustrated embodiment, stable electrical contact between plug member 4520 and contact member 200A may be enhanced by a snug fit (i.e. line-to-line or interference fit) between pin extension 402 and end 422 and/or by a weld joint, for example, being formed at 450, between end 422 and head 405. Alternately, or in addition, the fit of pin extension 402 within end 422 can increase the ease of assembly by holding plug member 4520 together with contact member 200A, prior to passing first terminal end 421 of contact member 200A into channel 310. Of course, plug member 4520 may also be employed with contact member 200B, in a manner similar to that described for contact member 200A.

According to some embodiments, the compression of each contact member 200A, 200B within the corresponding channel 310, via the corresponding fixed plug member 452, 4520, is sufficient to maintain stable electrical contact, between plug member 452, 4520 and the corresponding contact member 200A, 200B, without significantly increasing a force necessary to insert lead connector 130 (FIG. 1A) through connector bore 25 (and, likewise, another force to withdraw the lead connector from bore 25). That is, a stiffness of each mounted contact member 200A, 200B, which is held in place by the corresponding plug member 452, 4520, will be low enough to allow coiled wire 420, 520 to deform, along the corresponding contact surface 20A, 20B, when lead connector 130 is inserted (or withdrawn) through bore 25, without requiring an excessive insertion (or withdrawal) force, yet high enough to maintain stable electrical contact with the corresponding conductive surface 131 of inserted lead connector 130. An insertion force that is not excessive, according to some embodiments of the present disclosure, is no greater than approximately 0.26 pounds; and, for reliable electrical contact and continuity, according to some embodiments, a 'running' force of inserted lead connector 130 within bore 25 is no less than approximately 0.014 pounds. According to an exemplary embodiment, if an outer diameter of conductive surfaces 131 of lead connector 130 is approximately 0.05 inch, a gap G (FIGS. 4A-B), in between relaxed, or undeformed opposing contact surfaces 20A, is between approximately 0.043 inch and approximately 0.047 inch. Furthermore, it may be appreciated that the stiffness along contact surface 20A, 20B may be tailored to also facilitate wider tolerances on the diameters thereof and/or on an outer diameter of lead connector 130.

With further reference to FIGS. 3C-D, entryway 331 of each channel 310 is shown being formed as a counter bore in order to provide a shoulder 311, against which the corresponding plug member 452 abuts for coupling to mounting member 312. The location of shoulder 311 can determine how much contact member 200A, 200B may be compressed by plug member 452. For example, shoulder 311 may provide a hard stop for plug member 452 and thereby prevent an over-compression of contact member 200A, 200B when contact assembly 122A, 122B is being assembled. According to alternate embodiments, some or all of channels 310 do not include shoulder 311.

Returning now to FIG. 4C, wire 420 of resilient contact member 200A is shown being coiled to a first pitch P1, in proximity to first and second terminal ends 421, 422, and to a second pitch P2, along contact surface 20A, wherein second pitch P2 is greater than first pitch P1 so that a stiffness of contact member 200A, in proximity to terminal ends 421, 422, is greater than that along contact surface 20A. As mentioned above, a stiffness of contact member 200A should not cause excessive insertion forces, yet an increased stiffness may make contact member 200A more durable, over a life of a connector assembly in which contact assembly 122A is employed, for example, to prevent plastic deformation and/or dislodgement from and/or displacement within channel 310 as a result of multiple insertion and withdrawals of lead connectors. Thus, according to the illustrated embodiment of contact member 200A, the stiffness is increased in proximity to terminal ends 421, 422 of contact member 200A, via smaller first pitch P1, without impacting a stiffness along contact surface 20A. According to alternate embodiments, other means, for example, increasing a wire diameter or changing material properties of the wire, in proximity to terminal ends 421, 422, may be employed to increase the stiffness of contact member 200A in proximity to terminal ends 421, 422, while maintaining a relatively lower stiffness along contact surface 20A.

Turning to FIG. 5C, wire 520 of resilient contact member 200B is shown being coiled to various diameters. A first diameter D1, in proximity to first and second terminal ends 521, 522, is shown tapering down, along contact surface 20B, to a second diameter D2, wherein first diameter D1 is greater than second diameter D2. With reference to FIGS. 5A-B, in conjunction with FIG. 7, it may be appreciated that the tapering diameter of contact members 200B can provide for a more conformable interface for the insertion of lead connector 130 into bore 25. It should be noted that contact member 200B may also have a variable stiffness, similar to that described for contact member 200A, for example, achieved with a variable coil pitch, wire diameter and/or wire material properties. With further reference to FIGS. 5A-C, contact surface 20B defines a reduced diameter RD within bore 25, which reduced diameter RD is approximately concentric with the diameter of bore 25, and would be approximately concentric with an outer diameter of a conductive surface 131 of lead connector 130 (FIG. 1A) when inserted within bore 25. Thus, it may be appreciated that contact surface 20B can maximize the electrical contact interface with inserted conductive surface 131, for example, when compared to contact surface 20A of contact member 200A; furthermore, a clearance between diameter D2 of each contact member 200B and an inner diameter of the corresponding channel 310 of mounting member 312 can allow for greater outward deformation of contact member 200B when lead connector 131 is inserted in bore 25, thereby facilitating wider tolerances on an outer diameter of lead connector 130 and/or diameter D2 of contact member 200B. According to an exemplary embodiment, if an outer diameter of conductive surfaces 131 of lead connector 130 is approximately 0.05 inch, reduced diameter RD within bore, which is defined by opposing relaxed, or un-deformed contact surfaces 20B, is between approximately 0.043 inch and approximately 0.047 inch.

Figure 6A:
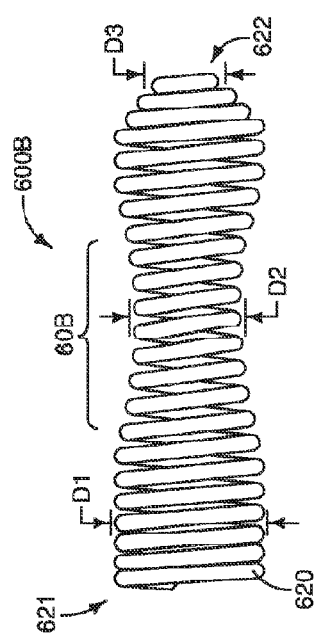
FIG. 6A is a plan view of a resilient contact member, according to yet further embodiments.
Figure 6B:
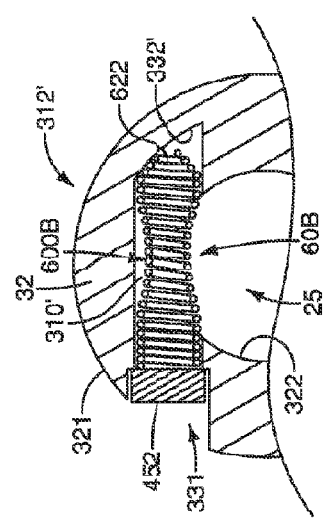
FIG. 6B is a cross-section through a portion of a contact assembly that includes the contact member of FIG. 6A, according to some embodiments.

FIG. 6A is a plan view of a resilient contact member 600B, according to yet further embodiments. FIG. 6A illustrates contact member 600B including a first terminal end 621 and a second terminal end 622, and being formed from a coiled wire 620 whose outer surface serves as a contact surface 60B, which is located between first and second terminal ends 621, 622. FIG. 6A further illustrates wire 620, similar to wire 520 of contact member 200B, being coiled to various diameters that include first and second diameters D1, D2, but, in contrast to contact member 200B, coiled wire 620 tapers down to a third diameter D3 at second terminal end 622 of contact member 600B. Diameter D3 is less than diameter D1 and may be equal to, less than, or greater than diameter D2. Contact member 600B may be particularly suitable for mounting in a modified mounting member 312', a portion of which is shown in the cross-section view of FIG. 6B. It should be noted that modified mounting member 312', according to some embodiments, includes the sidewall 32, that was previously described for mounting member 312, and four channels 310', which are arranged in a similar fashion to channels 310 of mounting member 312. FIG. 6B illustrates at least one of channels 310' including a beveled terminal surface 332' against which second terminal end 622 of the mounted contact member 600B abuts.

Figure 7:
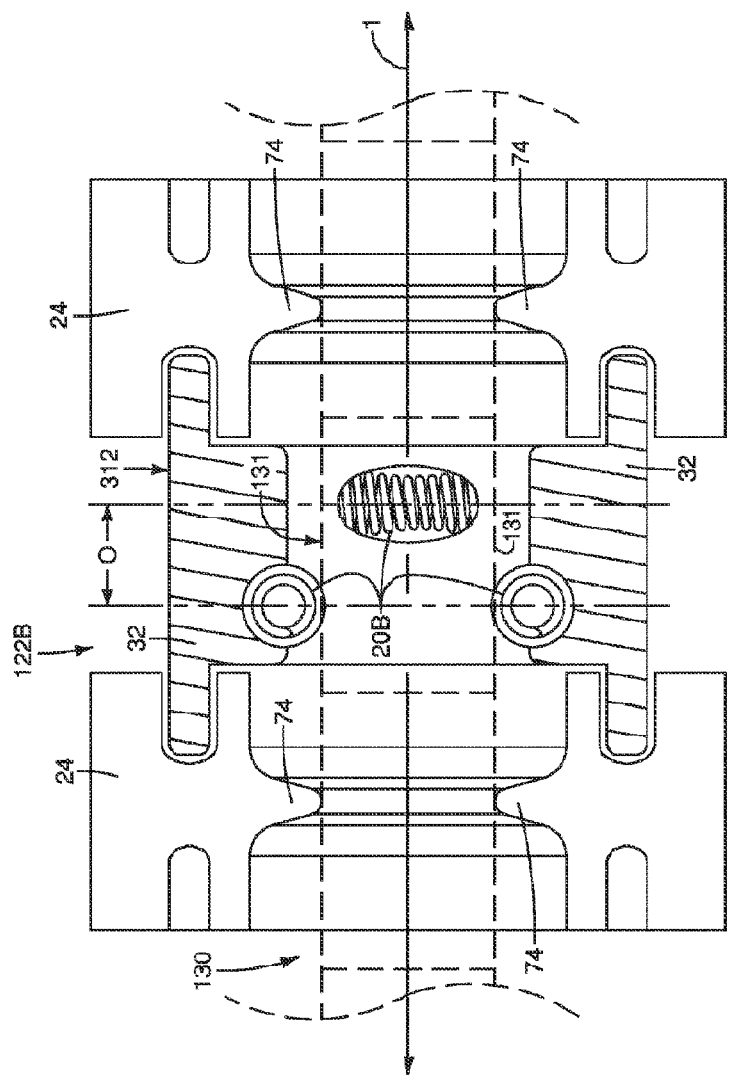
FIG. 7 is a longitudinal cross-section along a portion of a connector assembly, according to some embodiments.

FIG. 7 is a longitudinal cross-section along a portion of a connector assembly, for example, connector assembly 120 of FIG. 1B, that includes at least one of contact assemblies 122B. FIG. 7 illustrates seal members 24, each interlocking with an end of sidewall 32 of mounting member 312 in proximity to the corresponding counter bore 205 (FIG. 3B), which is defined by inner surface 322 of sidewall 32, as previously described in conjunction with FIG. 23. The illustrated interlocking features of connector assembly 120 are described in greater detail in commonly-assigned U.S. Pat. No. 6,895,276, relevant portions of which are hereby incorporated by reference. FIG. 7 further illustrates a portion of a lead connector (shown in phantom lines), for example, connector 130 (FIG. 1A), having been inserted into the connector assembly so that contact surfaces 20B of contact assembly 122B make contact with one of conductive surfaces 131, and sealing rings 74 of seal members 124 seal against surfaces of the insulative spacers of connector 130, which are located on either side of conductive surface 131.

Figure 8A:
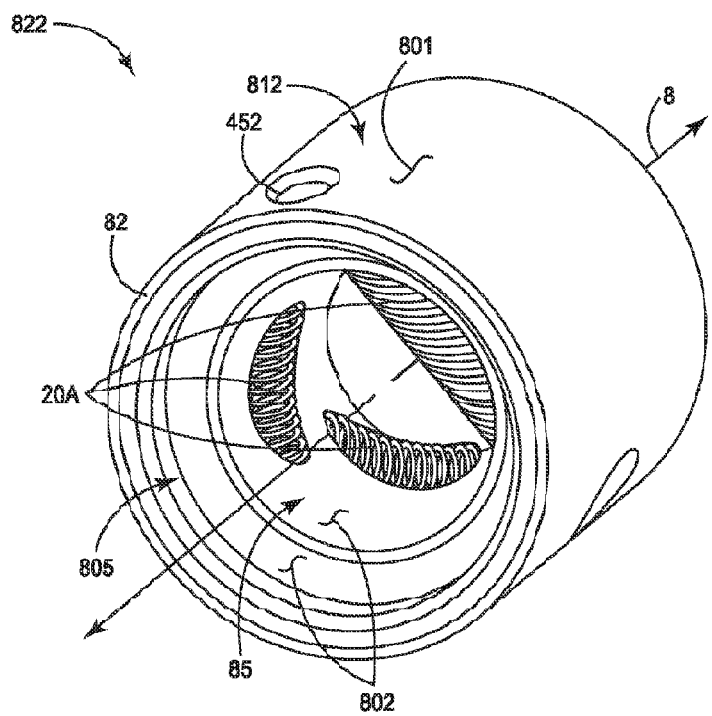
FIGS. 8A-B are perspective and section views of a contact assembly, according to some alternate embodiments.
Figure 8B:
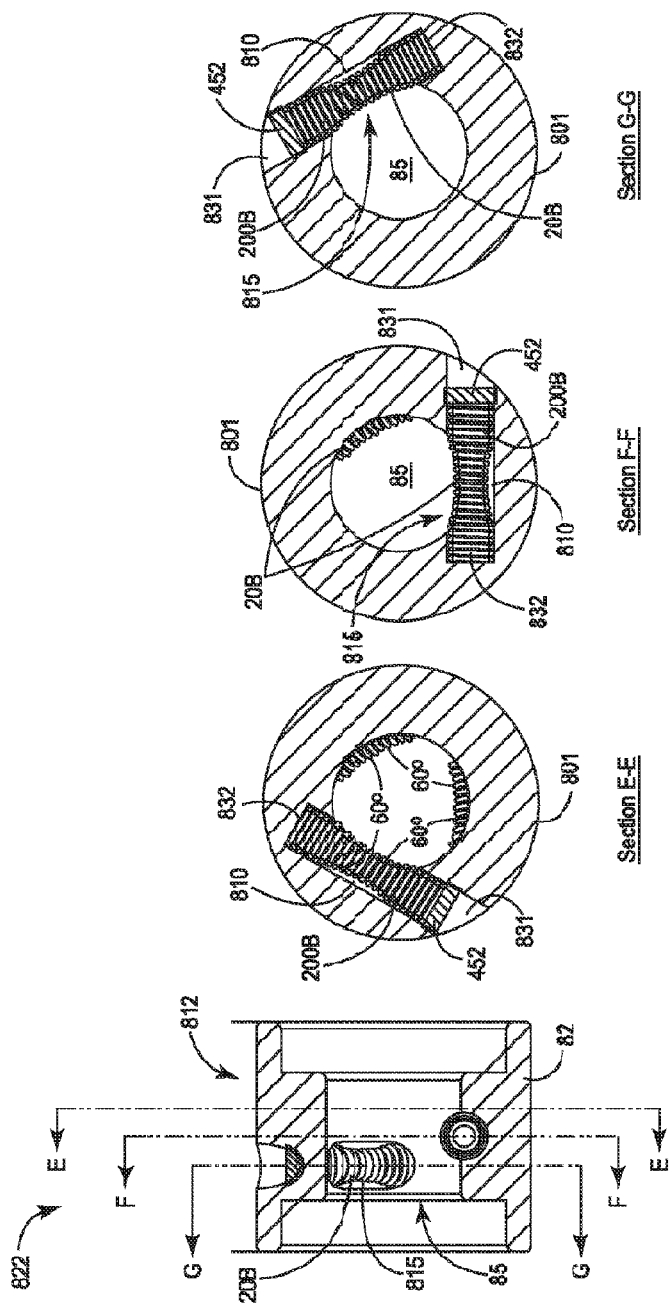

As mentioned above, alternative embodiments of contact assemblies may include a mounting member that has a different number and configuration of channels, than that previously described, for example, as illustrated in FIGS. 8A-B. FIG. 8A is a perspective view of contact assembly 822 and FIG. 8B is a series of cross-section views of contact assembly 822, according to some alternate embodiments. FIGS. 8A-B illustrate contact assembly 822 including a mounting member 812; mounting member 812 is shown including a sidewall 32, which has an outer surface 801 and an inner surface 802. Sidewall 82 of mounting member 812 may be formed from any suitable conductive material, examples of which include, without limitation, MP35N alloy, titanium and alloys thereof, tantalum and alloys thereof, platinum-iridium alloys and stainless steel. According to the illustrated embodiments, inner surface 802 defines a connector bore 85 and at least one counter bore 805; according to alternate embodiments, counter bore 805 need not be included. With reference back to FIGS. 1A-B, contact assembly 822 may be employed in place of any or all of contact assemblies 122 so that connector bore 85 is approximately aligned along one of module bores 121.

FIGS. 8A-B further illustrates three channels 810 formed in sidewall 82 and resilient contact members 200B mounted within channels 810, such that contact surfaces 20B are positioned to impose asymmetrical contact forces on an inserted lead connector. Like the previously described channels 310 of mounting member 312, each channel 810 includes an entryway 831, which is located at outer surface 801 of sidewall 82, a terminal surface 832 and an opening 815, which is located at inner surface 802 of sidewall 82, between entryway 831 and terminal surface 832, in order to expose the corresponding contact surface 20B of each mounted contact member 200B. According to the illustrated embodiment, each contact member 200B (or, alternately each contact member 200A) may be mounted in mounting member 812 via insertion into entryway 831 of one of channels 810, and once inserted, passed into the channel until a terminal end thereof abuts terminal surface 832, for example, as illustrated in FIG. 8B. Like contact assemblies 122A, 122B, plug members 452 are preferably employed to hold each contact member 200B within the corresponding channel 810, as previously described.

With further reference to FIGS. 8A-8B, channels 810 are oriented to surround a perimeter of bore, for example, in a footprint of an equilateral triangle, and are spaced apart from one another along a longitudinal axis 8 of contact assembly 822 so that openings 815 and exposed contact surfaces 20B are likewise spaced apart from one another along axis 8 by a distance S. According to some preferred embodiments, distance S is between approximately 0.010 inch and approximately 0.012 inch, so that, collectively, the three contact surfaces 20b of contact assembly 822 can provide a centering force for an inserted lead connector over a length that does not exceed approximately 0.025 inch.

In the foregoing detailed description of the disclosure, specific exemplary embodiments of the invention have been described. However, it may be appreciated that various modifications and changes can be made, without departing from the scope of the disclosure, as set forth in the appended claims.

We claim:

1. A contact assembly for a connector assembly of a medical device, the contact assembly comprising:
    a mounting member including a sidewall, the sidewall including an outer surface, an inner surface and a plurality of channels that are formed within the sidewall, between the inner and outer surfaces, the inner surface defining a connector bore that extends along a longitudinal axis of the mounting member, and each channel of the plurality of channels including an entryway a terminal surface and an opening, the entryway being located at the outer surface of the sidewall, and the opening being located between the entryway and the terminal surface, at the inner surface of the sidewall;
    a plurality of resilient contact members, each of the plurality of contact members extending from a first terminal end to a second terminal end and including a contact surface, the contact surface of each contact member being located between the first and second terminal ends thereof, and each contact member being mounted in a corresponding channel of the plurality of channels of the mounting member, such that the first terminal end of each contact member abuts the terminal surface of the corresponding channel, the second terminal end of each contact member is located within the corresponding channel, adjacent to the entryway thereof, and the contact surface of each contact member is exposed, through the opening of the corresponding channel, within the connector bore, for electrical coupling with a conductive surface of an elongate medical electrical lead connector that is inserted into the connector bore, along the longitudinal axis thereof; and
    a plurality of plug members, each plug of the plurality of plug members being fixed within the entryway of a corresponding channel, of the plurality of channels of the mounting member, and being electrically coupled to the sidewall of the mounting member and to the second terminal end of a corresponding contact member of the plurality of resilient contact members.

2. The contact assembly of claim 1, wherein each contact member of the plurality of resilient contact members comprises a coiled wire.

3. The contact assembly of claim 2, wherein an outer surface of each coiled wire comprises the contact surface of a corresponding contact member of the plurality of resilient contact members.

4. The contact assembly of claim 3, wherein each coiled wire has a first outer diameter, in proximity to each of the first and second terminal ends of the corresponding contact member, and a second outer diameter along the contact surface of the corresponding contact member, the second outer diameter being smaller than the first outer diameter.

5. The contact assembly of claim 4, wherein the first terminal end of each contact member is an extension of the corresponding coiled wire and has a third outer diameter, the third outer diameter being smaller than the first outer diameter.

6. The contact assembly of claim 3, wherein each coiled wire has a first pitch, in proximity to each of the first and second terminal ends of the corresponding contact member, and a second pitch at the contact surface of the corresponding contact member, the second pitch being greater than the first pitch.

7. The contact assembly of claim 1, wherein each channel of the plurality of channels of the mounting member extends across the longitudinal axis of the mounting member such that the entryway and the corresponding terminal surface of each channel are located on opposite sides of the longitudinal axis.

8. The contact assembly of claim 1, wherein the inner surface of the sidewall of the mounting member further defines one or two counter bores, each counter bore extending from a corresponding end of the connector bore.

9. The contact assembly of claim 1, wherein the opening of a first channel of the plurality of channels of the mounting member is located directly opposite the opening of a second channel of the plurality of channels.

10. The contact assembly of claim 9, wherein the opening of a third channel of the plurality of channels is located directly opposite the opening of a fourth channel of the plurality of channels.

11. The contact assembly of claim 10, wherein the openings of the first and second channels are offset, along the longitudinal axis of the mounting member, from the openings of the third and fourth channels.

12. The contact assembly of claim 1, wherein:
    the plurality of channels of the mounting member includes a first channel, a second channel and a third channel, each channel being oriented to surround a perimeter of the contact bore in a footprint of an equilateral triangle; and
    the openings of the first, second and third channels are spaced apart from one another along the longitudinal axis of the mounting member.

13. The contact assembly of claim 1, wherein the entryway of each channel of the plurality of channels includes a shoulder, and each plug member abuts the shoulder of the corresponding channel of the plurality of channels.

14. The contact assembly of claim 1, wherein one or all of the plurality of plug members includes a pin extension fitted within the second terminal end of the corresponding contact member of the plurality of resilient contact members.

15. A connector assembly for a connector module of a medical device, the connector assembly comprising the contact assembly, the contact assembly comprising:
    a mounting member including sidewall, the sidewall including an outer surface, an inner surface and a plurality of channels that are formed within the sidewall, between the inner and outer surfaces, the inner surface defining a connector bore that extends along a longitudinal axis of the mounting member, and each channel of the plurality of channels including an entryway a terminal surface and an opening, the entryway being located at the outer surface of the sidewall, and the opening being located between the entryway and the terminal surface, at the inner surface of the sidewall;

a plurality of resilient contact members, each of the plurality of contact members extending from a first terminal end to a second terminal end and including a contact surface, the contact surface of each contact member being located between the first and second terminal ends thereof, and each contact member being mounted in a corresponding channel of the plurality of channels of the mounting member, such that the first terminal end of each contact member abuts the terminal surface of the corresponding channel, the second terminal end of each contact member is located within the corresponding channel, adjacent to the entryway thereof, and the contact surface of each contact member is exposed, through the opening of the corresponding channel, within the connector bore, for electrical coupling with a conductive surface of an elongate medical electrical lead connector that is inserted into the connector bore, along the longitudinal axis thereof; and a plurality of plug members, each plug of the plurality of plug members being fixed within the entryway of a corresponding channel, of the plurality of channels of the mounting member, and being electrically coupled to the sidewall of the mounting member and to the second terminal end of a corresponding contact member of the plurality of resilient contact members, wherein the inner surface of the sidewall of the mounting member further defines one or two counter bores, each counter bore extending from a corresponding end of the connector bore and;

first and second seal members; wherein the inner surface of the sidewall of the mounting member defines two counter bores; the first seal member interlocks with the sidewall of the mounting member in proximity to a first of the two counter bores; and the second seal member interlocks with the sidewall of the mounting member in proximity to a second of the two counter bores.

16. A contact assembly for a connector assembly of a medical device, the contact assembly comprising:

a mounting member including a sidewall, the sidewall including an outer surface, an inner surface and a channel formed within the sidewall, between the inner and outer surfaces, the inner surface defining a connector bore that extends along a longitudinal axis of the mounting member, and the channel including an entryway a terminal surface and an opening, the entryway being located at the outer surface of the sidewall, and the opening being located between the entryway and the terminal surface, at the inner surface of the sidewall; and a resilient contact member extending from a first terminal end to a second terminal end and including a contact surface, the contact surface being located between the first and second, terminal ends, and the contact member being mounted in the channel of the mounting member, such that the first terminal end of the contact member abuts the terminal surface of the channel, and the contact surface of the contact member is exposed, through the opening of the corresponding channel, within the connector bore, for electrical coupling with a conductive surface of an elongate medical electrical lead connector that is inserted into the connector bore, along the longitudinal axis thereof;

wherein the contact member comprises a coiled wire and an outer surface of the coiled wire comprises the contact surface of the contact member; and the coiled wire has a first stiffness, in proximity to each of the first and second terminal ends of the contact member, and second stiffness along the contact surface, the first stiffness being greater than the second stiffness.

17. The contact assembly of claim 16, wherein the coiled wire has a first pitch, in proximity to each of the first and second terminal ends, and a second pitch along the contact surface, the second pitch being greater than the first pitch.

18. The contact assembly of claim 16, wherein the coiled wire has first outer diameter, in proximity to each of the first and second terminal ends, and a second outer diameter along the contact surface, the second outer diameter being smaller than the first outer diameter.

19. The contact assembly of claim 18, wherein the first terminal end of the contact member is an extension of the coiled wire and has a third outer diameter, the third outer diameter being smaller than the first outer diameter.

20. The contact assembly of claim 16, wherein the second terminal end of the contact member is located within the channel of the mounting member, adjacent to the entryway thereof, and further comprising a plug member, the plug member being fixed within the entryway of the channel and being electrically coupled to the sidewall of the mounting member and to the second terminal end of the contact member.

21. The contact assembly of claim 20, wherein the entryway of the channel includes a shoulder, and the plug member abuts the shoulder.

22. The contact assembly of claim 20, wherein the plug member includes a pin extension fitted within the second terminal end of the contact member.

23. A method for making a contact assembly for a connector assembly of a medical device, the method comprising:

passing a first terminal end of a resilient contact member into an entryway of a channel and through the channel until the first terminal end abuts a terminal surface of the channel, the channel being formed in a sidewall of a mounting member, the sidewall including an outer surface and an inner surface, the inner surface defining a bore of the mounting member, and the channel extending from the entryway thereof, located at the outer surface of the sidewall, to the terminal surface thereof, located within the sidewall, the channel including an opening into the bore of the mounting member, the opening being located between the entryway and the terminal surface; and coupling a plug member to the mounting member in proximity to the entryway of the channel, the plug member making electrical contact with a second terminal end of the contact member, the second terminal end being opposite the first terminal end of the contact member.

24. The method of claim 23, wherein coupling the plug member comprises laser welding.

25. The method of claim 23, further comprising coupling the plug member to the second terminal end of the contact member, in order to make the electrical contact therebetween, prior to passing the first terminal end of the contact member.

26. The method of claim 23, further comprising inserting a portion of the plug member into the second terminal end of the contact member, in order to make the electrical contact therebetween.

27. A contact assembly for a connector assembly of a medical device, the contact assembly comprising:

a mounting member including a sidewall, the sidewall including an outer surface, an inner surface and three channels that are formed within the sidewall, between the inner and outer surfaces, the inner surface defining a connector bore that extends along a longitudinal axis of the mounting member, and each channel including an entryway a terminal surface and an opening, the entryway being located at the outer surface of the sidewall, and the opening being located between the entryway and the terminal surface, at the inner surface of the sidewall; and three resilient contact members each formed by a coiled wire, each contact member extending from a first terminal end to a second terminal end and including a contact surface defined by an outer surface of the corresponding coiled wire between the first and second terminal ends thereof, and each contact member being mounted in a corresponding channel of the three channels of the mounting member, such that the first terminal end of each contact member abuts the terminal surface of the corresponding channel, the second terminal end of each contact member is located within the corresponding channel, adjacent to the entryway thereof, and the contact surface of each contact member is exposed, through the opening of the corresponding channel, within the connector bore, for electrical coupling with a conductive surface of an elongate medical electrical lead connector that is inserted into the connector bore, along the longitudinal axis thereof; and wherein each channel of the mounting member is oriented to surround a perimeter of the connector bore in a footprint of an equilateral triangle; and the openings of the first, second and third channels are spaced apart from one another along the longitudinal axis of the mounting member.

28. The contact assembly of claim 27, wherein each coiled wire has a first outer diameter, in proximity to each of the first and second terminal ends of the corresponding contact member, and a second outer diameter along the contact surface of the corresponding contact member, the second outer diameter being smaller than the first outer diameter.

29. The contact assembly of claim 28, wherein the first terminal end of each contact member is an extension of the corresponding coiled wire and has a third outer diameter, the third outer diameter being smaller than the first outer diameter.

30. The contact assembly of claim 27, wherein each coiled wire has a first pitch, in proximity to each of the first and second terminal ends of the corresponding contact member, and a second pitch at the contact surface of the corresponding contact member, the second pitch being greater than the first pitch.

31. A connector assembly for a connector module of a medical device, the connector assembly comprising at least two of the contact assemblies of claim 27.

* * * * *